US006676653B2

(12) United States Patent
Juhasz et al.

(10) Patent No.: US 6,676,653 B2
(45) Date of Patent: Jan. 13, 2004

(54) DEVICE AND METHOD FOR REMOVING GAS AND DEBRIS DURING THE PHOTODISRUPTION OF STROMAL TISSUE

(75) Inventors: Tibor Juhasz, Irvine, CA (US); Ronald M. Kurtz, Ann Arbor, MI (US)

(73) Assignee: IntraLase Corp., Irvine, CA (US)

( * ) Notice: Subject to any disclaimer, the term of this patent is extended or adjusted under 35 U.S.C. 154(b) by 23 days.

(21) Appl. No.: 10/008,947

(22) Filed: Dec. 6, 2001

(65) Prior Publication Data

US 2002/0087150 A1 Jul. 4, 2002

Related U.S. Application Data

(63) Continuation of application No. 09/266,453, filed on Mar. 11, 1999, now Pat. No. 6,344,040.

(51) Int. Cl.[7] .............................................. A61B 18/18
(52) U.S. Cl. ............................ 606/4; 606/6; 606/10; 606/17
(58) Field of Search ........................ 606/4–6, 10, 13, 606/17; 607/89, 91

(56) References Cited

U.S. PATENT DOCUMENTS

| 3,769,963 A | | 11/1973 | Goldman et al. | |
|---|---|---|---|---|
| 4,538,608 A | | 9/1985 | L'esperance, Jr. | |
| 4,660,556 A | | 4/1987 | Swinger et al. | |
| 4,729,372 A | | 3/1988 | L'esperance, Jr. | |
| 4,744,360 A | * | 5/1988 | Bath ............................ | 606/6 |
| 4,941,093 A | | 7/1990 | Marshall et al. | |
| 4,994,058 A | * | 2/1991 | Raven et al. .................. | 606/5 |
| 5,112,328 A | * | 5/1992 | Taboada et al. ............... | 606/4 |
| 5,336,215 A | | 8/1994 | Hsueh et al. | |
| 5,549,632 A | * | 8/1996 | Lai ............................... | 606/5 |
| 5,741,245 A | | 4/1998 | Cozean et al. | |
| 5,827,264 A | | 10/1998 | Hohla | |
| 6,342,053 B1 | | 1/2002 | Berry | |

OTHER PUBLICATIONS

Marshall, John et al.; Photoablative reprofiling of the cornea using an excimer laser: Photorefractive keratectomy; Lasers in Ophthamology, vol. 1, No. 1 pp. 21–48 (1986).
Habib, Maged S. M.D., et al., Mass Spectrometry Analysis of the Cavitation Bubbles By–Products of Intrastromal Photorefractive Keratectomy (IPRK) with the ND: YLF Picosecond Laser, pp. 1–8; Jul. 18, 1994.

* cited by examiner

Primary Examiner—Roy D. Gibson
(74) Attorney, Agent, or Firm—Fulbright & Jaworski L.L.P.

(57) ABSTRACT

A device for removing gas and debris from the stroma of an eye during ophthalmic laser surgery includes a contact lens that is formed with a recessed chamber. The device also includes a suction pump that is connected in fluid communication with the recessed chamber. In operation, the stroma is stabilized in the recessed chamber of the contact lens and an opening into the stroma is created. This opening is created either by the laser beam, or by a probe that is mounted on the contact lens to penetrate the stroma while the stroma is stabilized in the recessed chamber of the contact lens. Then, simultaneously or subsequently, as a laser beam is directed through the contact lens to photodisrupt tissue in the stroma the suction pump is activated to aspirate the resultant gas and debris through the opening and out of the stroma.

13 Claims, 2 Drawing Sheets

DEVICE AND METHOD FOR REMOVING GAS AND DEBRIS DURING THE PHOTODISRUPTION OF STROMAL TISSUE

This application is a continuation of application Ser. No. 09/266,453, filed Mar. 11, 1999, which has since issued as U.S. Pat. No. 6,344,040.

FIELD OF THE INVENTION

The present invention pertains generally to devices which are useful in ophthalmic laser surgery. More particularly, the present invention pertains to contact lenses which will stabilize the eye of a patient during ophthalmic surgery. The present invention is particularly, but not exclusively, useful as a contact lens which stabilizes the eye and also aspirates the gas and debris that is created as stromal tissue is photodisrupted during intrastroma ophthalmic laser surgery.

BACKGROUND OF THE INVENTION

During laser surgery, the interaction of the laser beam with body tissue involves a phenomenon which is generally referred to as photodisruption. The result of photodisruption on the affected tissue is really three-fold. In part, the tissue is vaporized. In part, there are mechanical effects on the tissue which become manifest in the tearing, separation and division of the affected tissue. Finally, there may be thermal effects which include charring and scorching of the affected tissue. The consequences are mixed. Along with the beneficial and intended consequences for a particular surgical procedure (i.e. the cutting or removing of tissue) there are also unwanted consequences of photodisruption. These unwanted consequences typically result from the generation of gas and tissue debris which have the potential to disrupt the surgical procedure. Preferably, the unwanted gas and debris can be removed from the surgical site.

For laser surgical procedures which are accomplished on external or exposed tissue, the problem of removing gas and debris from the surgical site is relatively easily solved. In this case, the gas will dissipate and the debris can be easily washed away or aspirated. The case is quite different, however, where internal tissue is involved. Specifically, in the case of intrastromal procedures wherein a specific volume of internal stromal tissue is to be photodisrupted, there is a real concern about how to best remove the unwanted gas and debris. Clearly, this gas and debris needs to be removed for several reasons. These reasons include: 1) the need to reduce the unwanted build up of gas pressure in the stroma during a surgical procedure; and, 2) the need to remove debris particles and obstructions which could otherwise interfere with the laser beam during subsequent photodisruption of additional stromal tissue. In order to address these needs, reliance on something more than the body's own ability to resorb the affected tissue is necessary.

In light of the above, it is an object of the present invention to provide a device which will effectively reduce the unwanted build up of gas pressure in the stroma during ophthalmic laser surgery. Another object of the present invention is to provide a device which will effectively remove debris particles and obstructions from the stroma which could otherwise interfere with the subsequent photodisruption of additional tissue. Yet another object of the present invention is to provide a device for removing the gas and debris that results during the photodisruption of stromal tissue which is easy to use, relatively simple to manufacture, and comparatively cost effective.

SUMMARY OF THE PREFERRED EMBODIMENTS

A device for removing gas and debris from the stroma of an eye during intrastromal ophthalmic laser surgery includes a contact lens and a suction apparatus which is interconnected with the contact lens. Further, the contact lens is formed with a recessed chamber, and the suction apparatus is connected in fluid communication with the recessed chamber. With this combination, when the recessed chamber of the contact lens is positioned over the eye, and the suction apparatus is activated, the cornea of the eye is drawn into the recessed chamber to hold the cornea against the contact lens. This action also stabilizes the eye during subsequent laser surgery.

Once the cornea of the eye has been stabilized by the contact lens, a laser source can be activated to generate a laser beam. For purposes of the present invention, this laser beam will be directed through the contact lens to perform the desired intrastromal ophthalmic laser surgery. When doing so, stromal tissue is photodisrupted by the laser beam in a predetermined manner. It is well known, however, that as stromal tissue is photodisrupted by a laser beam, gas and debris are formed as by-products in the stroma. To compensate for this result, and avoid the unwanted consequences which can ensue if nothing is done, the gas and debris need to be removed as quickly as possible. In accordance with the present invention, the removal of gas and debris from inside the stroma can be accomplished by aspiration in either of two ways. For both of these ways, a fluid communication channel into the stroma needs to be created.

With one embodiment of the present invention for removing gas and debris from the stroma during intrastromal ophthalmic laser surgery, the laser system itself is used to create an external opening into the stroma. Importantly, in addition to establishing a fluid communication channel with the interior of the stroma, this external opening needs to remain in fluid communication with the recessed chamber during the surgical procedure. Stated in the negative, the external opening into the stroma can not be created wherever there is a contact between the cornea and the contact lens that would obstruct the external opening. Then, with the opening undisturbed, subsequent activation of the laser system can be accomplished in a manner which will place the gas and debris that results from the photodisruption of tissue in fluid communication with the external opening. The external opening, of course, will also be in fluid communication with the recessed chamber, and the recessed chamber will be in fluid communication with the suction apparatus. Accordingly, the suction apparatus can aspirate the gas and debris from the stroma and thereby remove this material from the eye.

With another embodiment of the present invention for removing gas and debris from the stroma during intrastromal ophthalmic laser surgery, a hollow probe is mounted on the contact lens to extend into the recessed chamber. Thus, for this embodiment of the present invention, the suction apparatus is connected in fluid communication with the recessed chamber through the probe. With this configuration, when the recessed chamber of the contact lens is positioned over the cornea, and the suction device is activated to draw the cornea into the recessed chamber, the probe will penetrate into the stroma. Subsequent activation of the laser system will then need to begin at the tip of the probe and continue from there through the stroma as desired. In this manner, the tip of the probe will remain in fluid communication with the stromal tissue that is being photodisrupted so that the resultant gas and debris can be removed from the eye.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
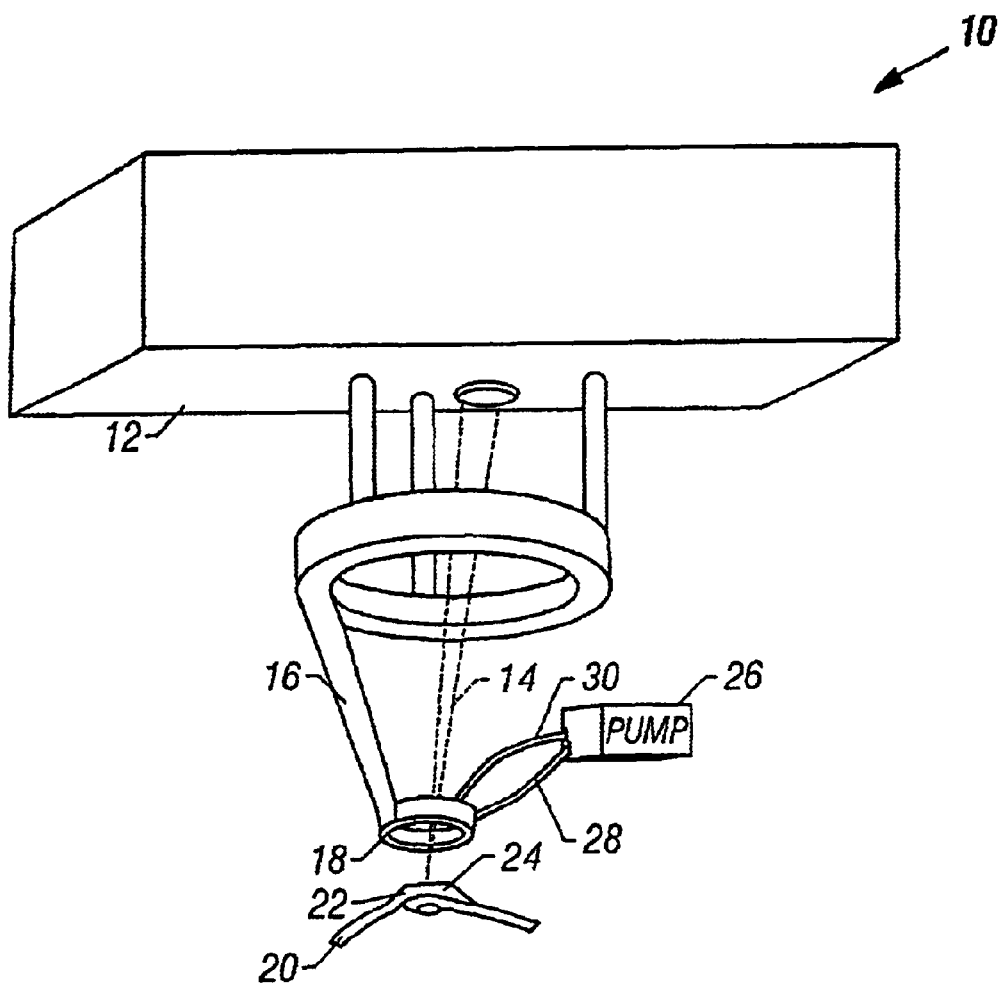
FIG. 1 is a perspective view of the device for removing gas and debris from the stroma in accordance with the present invention.

Referring initially to FIG. 1, a device for removing gas and debris from the eye during intrastromal ophthalmic laser surgery is shown and generally designated 10. As shown, the device 10 includes a laser system 12 which is used to generate a laser beam 14 that can be used for the particular surgical procedure that is to be performed. As intended for the present invention, the laser beam 14 will preferably be a pulsed laser beam which includes a train of pulses. Further, depending on the particular surgical procedure that is to be performed, and the desires of the attending physician, the wavelength for light in the laser beam 14 can be selected from several ranges of wavelengths, and each pulse in the beam 14 can have a duration that is in the range of picoseconds or femtoseconds. FIG. 1 also shows that the device 10 includes a retainer 16 which is used to hold a contact lens 18 in a predetermined spatial relationship with the laser system 12. For purposes of the present invention, the contact lens 18 is preferably a rigid structure which is made of glass or a clear medical grade plastic.

As intended for the present invention, the laser beam 14 is directed through the contact lens 18 and toward the eye 20 of a patient. More specifically, the laser beam 14 is directed into the stroma 22 of the cornea 24 of eye 20, where its focal point is moved along a predetermined path to photodisrupt stromal tissue. As mentioned above, the by-products of this photodisruption include gas and debris which needs to be removed from the stroma 22.

Figure 2:
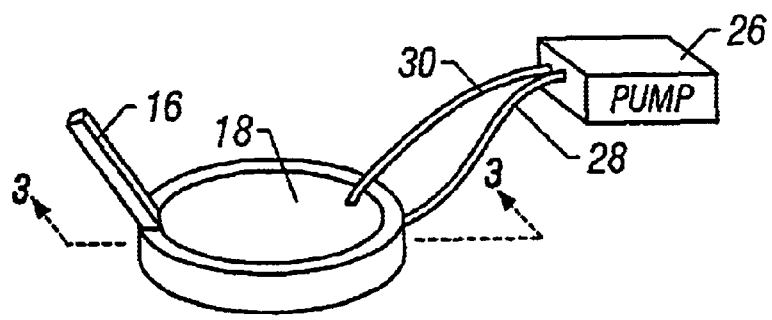
FIG. 2 is a perspective view of the contact lens and suction apparatus of the present invention, shown detached and isolated from the laser system.

In both FIGS. 1 and 2 it will be seen that the device 10 also includes a suction pump 26 which is connected in fluid communication with the retainer 16 by a first suction line 28. Additionally, FIGS. 1 and 2 shown that the device 10 may include a second suction line 30 which directly connects the suction pump 26 in fluid communication with the contact lens 18. The particulars of these connections, and the detailed structure of the contact lens 18 will be best appreciated by reference to FIGS. 3A, 3B, 4A and 4B.

Figure 3A:
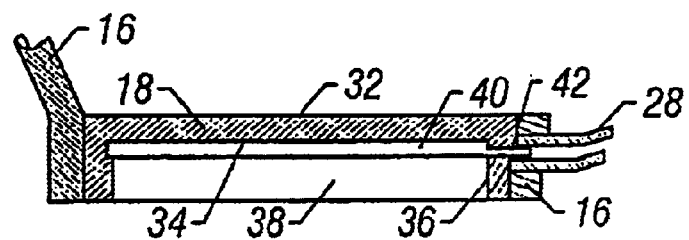
FIG. 3A is a cross sectional view of the contact lens of one embodiment of the present invention as seen along the line 3—3 in FIG. 2.

FIG. 3A shows that a contact lens 18 in accordance with the present invention has a substantially flat anterior surface 32, and a substantially flat aplanation surface 34. As shown, the anterior surface 32 is generally parallel to the aplanation surface 34. It is to be appreciated, however, that for an alternate embodiment of the present invention, the anterior surface 32 and the aplanation surface 34 may be curved to conform with the radius of curvature of the eye. In any event, the resultant optical interaction between these surfaces 32, 34 is the same for all configurations. Additionally, FIG. 3A shows that the contact lens 18 includes a skirt 36 which extends outwardly from the aplanation surface 34, and surrounds the aplanation surface 34 to define a recessed chamber 38 which is located between the aplanation surface 34 and the skirt 36. In further detail, FIG. 3A shows that in the recessed chamber 38 at the interface between the skirt 36 and the aplanation surface 34, the contact lens 18 is formed with a groove 40.

Figure 3B:
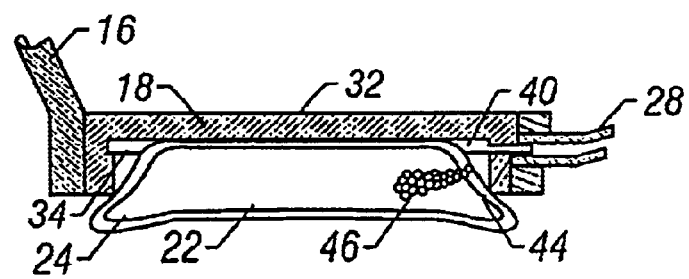
FIG. 3B is a view of the contact lens as seen in FIG. 3A with the contact lens in contact with the cornea of an eye.

Still referring to FIG. 3A, it will be seen that the first suction line 28 is connected with the retainer 16 and is placed in fluid communication with the groove 40 in recessed chamber 38 via a passageway 42. With this connection it will be appreciated that the suction pump 26 is also in fluid communication with the recessed chamber 38. Accordingly, when the contact lens 18 is positioned on the eye 20 with the recessed chamber 38 against the cornea 24, and a partial vacuum is drawn in the recessed chamber 38 by the suction pump 26, the cornea 24 will be drawn toward and flattened against the aplanation surface 34 of the lens 18 substantially as shown in FIG. 3B. In this configuration (FIG. 3B), intrastromal ophthalmic laser surgery can be performed on the stroma 22.

As suggested in FIG. 3B, with the cornea 24 stabilized in recessed chamber 38 of contact lens 18, an external opening 44 in the anterior surface of cornea 24 can be made which will establish fluid communication with the interior of the stroma 22. Accordingly, as intrastromal laser surgery proceeds into the stroma 22 from external opening 44, the gas and debris 46 which results from photodisruption of the stromal tissue will be aspirated by the action of the suction pump 26. Specifically, for this embodiment of the device 10, the gas and debris 46 from inside the stroma 22 will be aspirated through the external opening 44 and into the recessed chamber 38. The gas and debris 46 will then be further aspirated from the recessed chamber 38 through the passageway 42 and first suction line 28 into a collection vial (not shown) in the suction pump 26. As will be appreciated by the skilled artisan, for this embodiment of the present invention, it is important that the opening 44 remain in fluid communication with the recessed chamber 38. This condition can, of course, be insured by first stabilizing the contact lens 18 on the eye 20, and then appropriately selecting the location for the external opening 44 on a portion of the anterior surface of the cornea 24 that is not in direct contact with the lens 18.

Figure 4A:
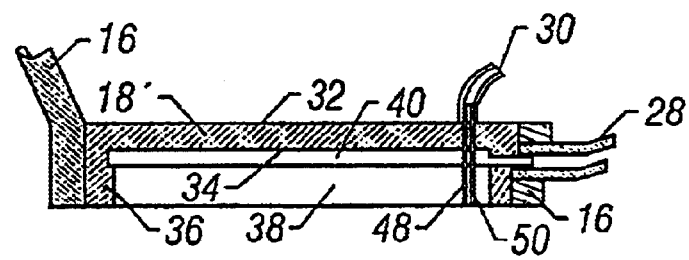
FIG. 4A is a cross sectional view of another embodiment of the contact lens of the present invention as seen along the line 3—3 in FIG. 2.
Figure 4B:
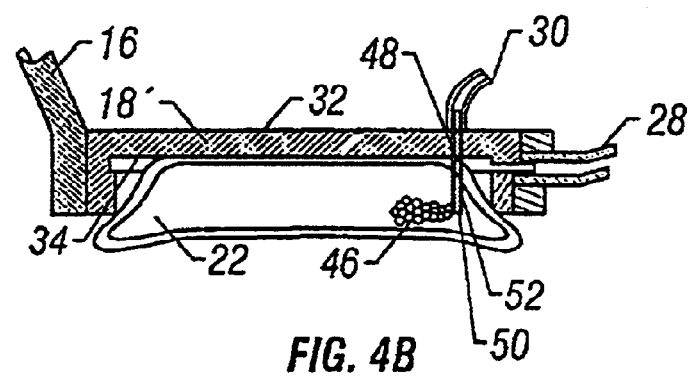
FIG. 4B is a view of the contact lens as seen in FIG. 4A with the contact lens in contact with the cornea of an eye.

Another embodiment for the contact lens 18' of the present invention is shown in FIG. 4A. The specific difference between the contact lens 18 of FIG. 3A, and the contact lens 18' of FIG. 4A, is that for the embodiment shown in FIG. 4A, there is a second suction line 30 which is connected in fluid communication with a hollow probe 48. More specifically, as shown in FIG. 4A, the probe 48 is mounted on the contact lens 18' to extend from the aplanation surface 34 and into the recessed chamber 38. Accordingly, when the contact lens 18' is positioned over the eye 20, and the suction pump 26 is activated to create a partial vacuum in the recessed chamber 38, the cornea 24 will be drawn into the recessed chamber 38. This will then cause the tip 50 of probe 48 to puncture or penetrate the anterior surface of the cornea 24. With this penetration, the tip 50 of probe 48 creates an external opening 52 through which it will become embedded into the stroma 22. Because the probe 48 is hollow, the suction pump 26 is in direct fluid communication with the exposed tip 50 of probe 48. Consequently, by beginning an intrastromal laser surgery at the tip 50, and thereafter progressing contiguously therefrom through the stroma 22, any gas and debris 46 which is created during surgery can be effectively aspirated. Specifically, this gas and debris 46 will be aspirated through the probe 48, and through the second suction line 30, back to a collection vial (not shown) in the suction pump 26.

While the particular Device and Method for Removing Gas and Debris During the Photodisruption of Stromal Tissue as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for removing gas and debris from inside the stroma of an eye caused by the photodisruption of stromal tissue during ophthalmic laser surgery, said system comprising:

a contact lens for stabilizing the cornea of an eye;

a laser for generating a laser beam, said laser beam being directed through said contact lens to photodisrupt tissue in the stroma of the cornea; and at least one of the laser or a non-laser cutter adapted to form an external opening into the stroma to access the gas and debris inside the stroma of an eye caused by the photodisruption of tissue.

2. The system of claim 1, further including a suction apparatus positioned in fluid communication with the external opening.

3. The system of claim 2, wherein said contact lens is formed with a recessed chamber.

4. The system of claim 2, wherein the contact lens comprises:

a lens member having an anterior surface and an aplanation surface, the aplanation surface being substantially parallel to the anterior surface;

a skirt surrounding the aplanation surface and extending outwardly therefrom to define a recessed chamber therebetween;

a passageway positioned substantially adjacent to said aplanation surface, said passageway in fluid communication with said recessed chamber; and a first suction line for connecting the suction apparatus in fluid communication with the passageway to create a partial vacuum in said recessed chamber to stabilize the cornea against the aplanation surface.

5. The system of claim 4, wherein said non-laser cutter is a probe, the probe being mounted on the contact lens, and wherein the system further comprises a second suction line for connecting the probe in fluid communication with the suction apparatus.

6. The system of claim 4, wherein the passageway is a groove formed in the skirt.

7. The system of claim 4, wherein the laser is programmed to form the external opening and the suction apparatus is in fluid communication with the passageway of the contact lens, the passageway is in fluid communication with the recessed chamber, and the recessed chamber is in fluid communication with the external opening into the stroma, such that the gas and debris from the stroma are aspirated through the external opening.

8. The system of claim 1, wherein said contact lens is formed with a recessed chamber.

9. The system of claim 1, wherein said laser is programmed to form the external opening.

10. A system for removing gas and debris caused by the photodisruption of stromal tissue during ophthalmic laser surgery, said system comprising:

a contact lens for receiving and stabilizing the cornea of an eye;

a laser system for generating a laser beam, said laser beam being directed through said contact lens to photodisrupt tissue in the stroma of the cornea; and a probe for creating an external opening into the stroma to access the gas and debris caused by the photodisruption of tissue.

11. A method for removing gas and debris from the stroma caused by the photodisruption of stromal tissue during ophthalmic laser surgery, said method comprising the steps of:

stabilizing the cornea of an eye with a contact lens;

activating a laser system to generate a laser beam, the laser beam being directed through the contact lens to photodisrupt tissue in the stroma of the cornea; and creating an external opening into the stroma to access the gas and debris caused by the photodisruption of tissue.

12. The method of claim 11, wherein said creating step is accomplished using the laser system.

13. The method of claim 11, wherein said creating step is accomplished using a probe mounted on the contact lens with the probe extending through the contact lens.

* * * * *